US006376684B1

(12) United States Patent
Senanayake et al.

(10) Patent No.: US 6,376,684 B1
(45) Date of Patent: Apr. 23, 2002

(54) STEREOSELECTIVE PROCESS FOR ALKYL PHENYLGLYCOLIC ACIDS

(75) Inventors: Chris Hugh Senanayake, Shrewsbury; Paul T. Grover, Marlborough, both of MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

(21) Appl. No.: 09/711,776

(22) Filed: Nov. 13, 2000

Related U.S. Application Data

(62) Division of application No. 09/187,832, filed on Nov. 6, 1998, now Pat. No. 6,180,823.

(51) Int. Cl.$^7$ .............................................. C07D 307/93
(52) U.S. Cl. ..................... 549/450; 562/470; 562/491; 562/489; 562/468
(58) Field of Search ................................. 562/489, 470, 562/491, 468; 549/450

(56) References Cited

U.S. PATENT DOCUMENTS

| | | | |
|---|---|---|---|
| 5,262,566 A | * 11/1993 | Mohrs et al. | ............... 562/468 |
| 5,750,540 A | 5/1998 | Tsuchiya et al. | ............ 514/318 |
| 5,948,792 A | 9/1999 | Tsuchiya et al. | ............ 514/317 |
| 5,973,182 A | 10/1999 | Bakale et al. | ................ 558/267 |
| 6,025,177 A | 2/2000 | Senanayake et al. | ........ 435/195 |
| 6,028,177 A | * 2/2000 | Senanayake et al. | ........ 435/195 |
| 6,090,971 A | * 7/2000 | Bakale et al. | .................. 560/40 |
| 6,140,529 A | * 10/2000 | Bakale et al. | .................. 560/58 |
| 6,180,823 B1 | * 1/2001 | Senanayake et al. | ........ 562/489 |

FOREIGN PATENT DOCUMENTS

WO   WO9805641   2/1998

OTHER PUBLICATIONS

Fráter et al. "Synthesis of Enantiomerically Enriched Atrolactic Acid and Other . . . " *Tetrahedron Letters* 22, 4221–4224 (1981).
Nelson "Catalyzed enantioselective aldol additions of latent enolate equivalents" *Tetrahedron: Asymmetry* 9, 357–359 (1998).
Seebach et al. "α–Alkylation of α–Heterosubstituted Carboxylic Acids Without Racemization" *Tetrahedron* 40, 1313–1324 (1984).
Polonski Conformational Dependence of the Circular Dichroism of 1,3–Dioxolan–4–Ones *Tetrahedron* 39, 3131–3137 (1983).
Visser et al., "Steroselective Synthesis and Biodistribution of Potent [$^{11}$C]–Labeled Antagonists for Positron Emission Topmography Imaging of Muscarine Receptors in the Airways," *J.Med.Chem.*, 40:117–27 (1997).
Seebach, D. and Naef, R., "274. Enantioselective Generation and Diastereoselcetive Reactions of Chiral Enaolates Derived from α–Heterosubstituted Carboxylic Acids," *Helvetica Chimica Acta*, 64:2704–08 (1981).
Pailer et al., "Derivate des 1,3–Dioxolan–4–ons und des 1,3–Oxathiolan–5–ons," *Montshefte für Chemie*, 99:891–901 (1968).
Inch et al. "Asymmetric Synthesis. Part III. Stereospecific Synthesis of (R)–2–Hydroxy–2–phenylpropionic . . . " *J. Chem. Soc. (C)*, Part II, 1041–2128 (1968).
Solomons, T.W. Graham *Organic Chemistry*, p. 213.
Visser et al, Stereoselective Synthesis & Biodistribution of Potent(11C)–Labeled Antagonist, Jan. 1997, American Chemical Soc., vol. 40, pp. 117–123.*

* cited by examiner

*Primary Examiner*—Paul J. Killos
*Assistant Examiner*—Taylor V. Oh
(74) *Attorney, Agent, or Firm*—Heslin Rothenberg Farley & Mesiti P.C.

(57) ABSTRACT

A process for preparing an alkyl phenylglycolic acid is disclosed. It follows the sequence of condensing a substituted acetaldehyde with mandelic acid to provide a 5-phenyl-1,3-dioxolan-4-one, which is condensed with an alkyl ketone or aldehyde to provide a 5-(1-hydroxyalkyl)-5-phenyl-1,3-dioxolan-4-one, which is dehydrated to a 5-(1-alkenyl)-5-phenyl-1,3-dioxolan-4-one. The 5-(1-alkenyl)-5-phenyl-1,3-dioxolan-4-one may be hydrolyzed and reduced to an α-alkylphenylglycolic acid or the hydrolysis and reduction steps may be reversed. The process enables the production of single enantiomers of cyclohexylphenylglycolic acid (CHPGA). An analogous process for racemic CHPGA is disclosed employing racemic mandelic acid and acetone. Novel intermediates in the process are also disclosed.

6 Claims, No Drawings

STEREOSELECTIVE PROCESS FOR ALKYL PHENYLGLYCOLIC ACIDS

CROSS REFERENCE TO RELATED APPLICATIONS

This application is a divisional of us application, Ser. No. 09/187,832, filed Nov. 6, 1998 now U.S. Pat. No. 6,180,823 the entire disclosure of which is incorporated herein by reference.

FIELD OF THE INVENTION

The invention relates to a chemical process for preparing α-alkylphenylglycolic acids and to intermediates in that process.

BACKGROUND OF THE INVENTION

Cyclohexylphenyl glycolic acid (also referred to herein as "CHPGA") is used as a starting material for manufacturing compounds that have important biological and therapeutic activities. Such compounds include, for example, oxphencyclimine, oxyphenonium bromide, oxypyrronium bromide, oxysonium iodide, oxybutynin (4-diethylamino-2-butynyl phenylcyclohexylglycolate) and its metabolites, such as desethyloxybutynin (4-ethylamino-2-butynyl phenylcyclohexylglycolate).

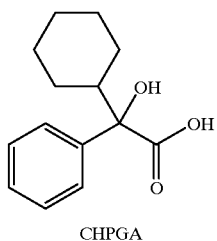

CHPGA

The important relation between stereochemistry and biological activity is well known. For example, the (S)-enantiomers of oxybutynin and desethyloxybutynin have been shown to provide a superior therapy in treating urinary incontinence, as disclosed in U.S. Pat. Nos. 5,532,278 and 5,677,346. The (R) enantiomer of oxybutynin has also been suggested to be a useful drug candidate. [Noronha-Blob et al., *J. Pharmacol. Exp. Ther*. 256, 562–567 (1991)].

Racemic CHPGA is generally prepared by one of two methods: (1) selective hydrogenation of phenyl mandelic acid or of phenyl mandelate esters, as shown in Scheme 1; or (2) cyclohexyl magnesium halide addition to phenylglyoxylate as shown in Scheme 2.

Scheme 1

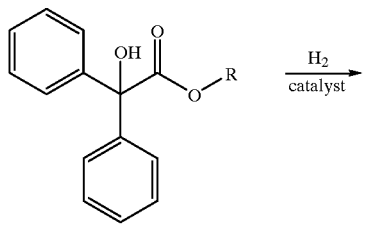

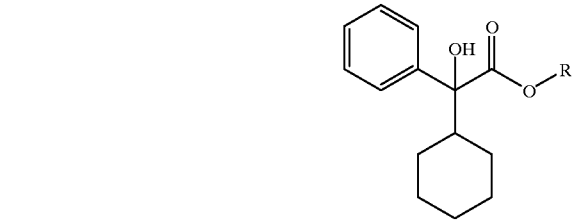

R is hydrogen or lower alkyl.

Scheme 2

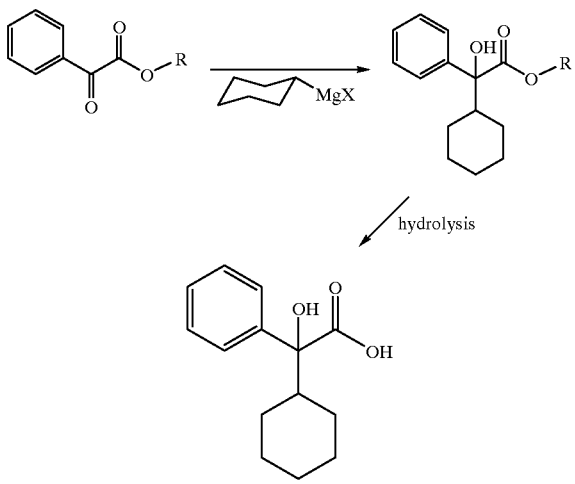

Asymmetric synthesis of individual enantiomers of CHPGA has been approached along the lines of Scheme 2, by Grignard addition to a chiral auxiliary ester of glyoxylic acid to give a diastereomeric mixture of esters. In addition, a multiple step asymmetric synthesis of (R)-CHPGA from (D)-arabinose using Grignard reagents has been reported.

As outlined in Scheme 3 below, the simple chiral ester wherein R* is the residue of a chiral alcohol, can be directly converted to chiral drugs or drug candidates by trans-esterification (R'=acetate), or hydrolyzed to yield chiral CHPGA and then esterified (R'=H).

Scheme 3

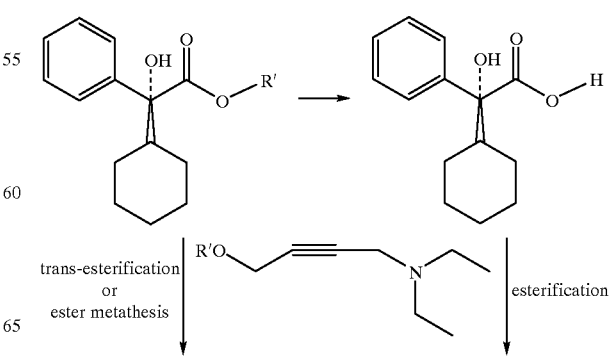

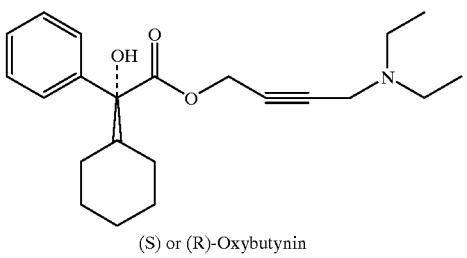

(S) or (R)-Oxybutynin

While the aforementioned asymmetric synthetic methods are adequate for many purposes, the chemical yields are in some cases poor, and the stereoselectivity is not always high. Also, the chiral auxiliary reagents that give good yields and higher stereoselectivity are often quite expensive. Thus, these processes are often cost prohibitive for use in commercial scale production of chiral pharmaceutical compounds.

A potential alternative to asymmetric synthesis is resolution of racemic CHPGA. This has been accomplished on an analytical scale using resolving agents such as ephedrine, quinine, and (+) and (−)-amphetamine. However, such resolving agents are expensive, making known processes for resolution as impractical as known asymmetric syntheses. In addition, resolution processes using these agents provide poor stereoselectivity. The poor stereoselectivity necessitates multiple recrystallization steps to isolate the single CHPGA enantiomer, which adds to the production costs of chiral pharmaceuticals made from these precursors.

A more efficient and economic method for producing α-alkylphenylglycolic acids, particularly single enantiomers of α-alkylphenylglycolic acids, on an industrial scale is therefore desirable. Such a method should provide high purity compounds in high chemical yields with few processing steps.

SUMMARY OF THE INVENTION

The above need is satisfied, the limitations of the prior art overcome, and other benefits realized in accordance with the principles of the present invention, which in one aspect relates to a process for preparing an alkyl phenylglycolic acid enriched in one enantiomer, comprising the sequential steps of:

(a) condensing a substituted acetaldehyde with a single enantiomer of mandelic acid to provide a 5-phenyl-1,3-dioxolan-4-one;

(b) condensing said 5-phenyl-1,3-dioxolan-4-one with an alkyl ketone or aldehyde to provide a 5-(1-hydroxyalkyl)-5-phenyl-1,3-dioxolan-4-one;

(c) exposing said 5-(1-hydroxyalkyl)-5-phenyl-1,3-dioxolan-4-one to dehydrating conditions to provide a 5-(1-alkenyl)-5-phenyl- 1,3-dioxolan-4-one;

(d) hydrolyzing said 5-(1-alkenyl)-5-phenyl-1,3-dioxolan-4-one to provide an α-alkenylphenylglycolic acid; and (e) reducing said α-alkenylphenylglycolic acid to an α-alkylphenylglycolic acid.

In an alternative embodiment, the last two steps (hydrolysis and reduction) can be reversed:

(d) reducing said 5-(1-alkenyl)-5-phenyl-1,3-dioxolan-4-one to provide a 5-alkyl-5-phenyl-1,3-dioxolan-4-one; and (e) hydrolyzing said 5-alkyl-5-phenyl-1,3-dioxolan-4-one to an α-alkylphenylglycolic acid.

In particular, preferred embodiments, the substituted acetaldehyde is pivaldehyde, the alkyl ketone is cyclohexanone, the mandelic acid is (S)-(+)-mandelic acid or (R)-(−)-mandelic acid and cyclohexylphenylglycolic acid enriched in either the S or the R enantiomer, respectively, is produced.

In another aspect, the invention relates to a process for preparing a racemic alkyl phenylglycolic acid, comprising a first step of:

(a) condensing acetaldehyde or a symmetrical dialkyl ketone with racemic
mandelic acid to provide a 5-phenyl-1,3-dioxolan-4-one;

followed by the same process described above for single enantiomers. The condensation of the acetaldehyde, symmetrical dialkyl ketone or substituted acetaldehyde with mandelic acid may be accomplished in the presence of an acid catalyst; the condensation of the 5-phenyl-1,3-dioxolan-4-one with an alkyl ketone or aldehyde may be accomplished under basic conditions.

In another aspect, the invention relates to a compound chosen from the group consisting of:

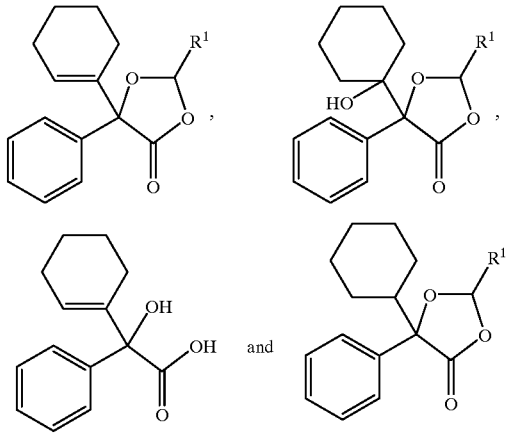

wherein R1 is alkyl of 1 to 10 carbons or substituted alkyl of 4 to 20 carbons in total. The compounds are novel intermediates in the synthesis of CHPGA.

DETAILED DESCRIPTION

The graphic representations of racemic, ambiscalemic and scalemic or enantiomerically pure compounds used herein are taken from Maehr J. Chem. Ed. 62, 114–120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. Thus, for example, the formula 5 is intended to encompass either one of the optically pure 5-cyclohexyl-5-phenyldioxol-2-ones:

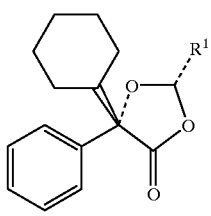

means a pure optical isomer which is one or the other of

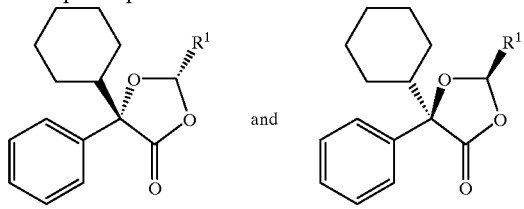

The term "enantiomeric excess" is well known in the art and is defined for a resolution of ab→a+b as $$ee_a = \left(\frac{\text{conc. of } a - \text{conc. of } b}{\text{conc. of } a + \text{conc. of } b}\right) \times 100$$

The term "enantiomeric excess" is related to the older term "optical purity" in that both are measures of the same phenomenon. The value of ee will be a number from 0 to 100, zero being racemic and 100 being pure, single enantiomer. A compound which in the past might have been called 98% optically pure is now more precisely described as 96% ee.; in other words, a 90% e.e. reflects the presence of 95% of one enantiomer and 5% of the other in the material in question. The term "diastereomeric excess (d.e.) is similarly defined as $$de_p = \left\{\frac{\text{conc. of } p - \text{conc. of } q}{\text{conc of } p + \text{conc of } q}\right\} \times 100$$

in which p and q are diastereomers, and 90% de reflects 95% of p and 5% of q. The diastereomeric excess is a measure of the diastereoselectivity of a reaction or process.

"Substituted acetaldehyde" means acetaldehyde in which one or more hydrogens is replaced so as to provide an aldehyde which, when incorporated into the dioxolone ring, is base-inert. For syntheses in which enantioselectivity is important, a bulky, base-inert aldehyde is needed. A "bulky, base-inert aldehyde" as the term is used herein refers to an aldehyde which meets two criteria: (1) it has sufficient steric bulk such that the approach of a ketone to the dioxolone anion 7 results in a product alcohol which is not a 1:1 mixture of enantiomers at the C-5 carbon; and (2) it contains

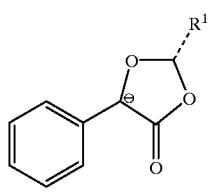

no substituents that, by virtue of their reactivity with base, prevent the formation of an anion at C-5 of the dioxolone. Aldehydes that meet these criteria are easily determined by the artisan by simply reacting the putative aldehyde with S-mandelic acid and then with cyclohexanone under the conditions described below and examining the $^1$H NMR for the signal of the proton at C-2; if there is a single pair of signals of equal integrated signal strength between 5 and 6 δ, the aldehyde fails criterion (1); if there is no signal between 5 and 6 δ, the aldehyde fails criterion (2); if there is more than one signal of non-equal integrated signal strength between 5 and 6 δ, the aldehyde meets the criteria; if there is only a single signal between 5 and 6 δ, the aldehyde not only meets the criteria, but is preferred. Examples of substituted acetaldehydes that are bulky and "base-inert" include pivaldehyde and diphenylacetaldehyde. Generally, "substituted acetaldehydes" include acetaldehydes in which at least two hydrogens on the α-carbon are replaced by alkyl or aryl groups, although we have found that if the two alkyl groups are no more bulky than methyls (isobutyraldehyde), the resulting dioxolone does not have a sufficient directing effect at C-5 to allow high enantioselectivity.

"Alkyl", as used herein, refers to saturated hydrocarbon residues containing twenty or fewer carbons in straight or branched chains, as well as monocyclic structures of 3 to 8 carbons and decalin. "Aryl" includes phenyl, naphthyl, and phenyl substituted with one or more alkyl or alkoxyl.

Symmetrical dialkyl ketones include acetone and diethyl ketone. The person of skill will readily appreciate that an equivalent to the foregoing ketones and aldehydes would be the corresponding acetals, such as acetone dimethyl acetal (dimethoxypropane), which are often commercially available. These would be converted to the dioxolone tinder analogous conditions by alcohol exchange.

The processes of the invention are illustrated in Schemes 4 and 5 using cyclohexanone as the exemplary alkyl ketone. Scheme 4 depicts the process in which the 5-cyclohexenyl-5-phenyldioxol-2-one 3 is first cleaved to α-cyclohexenylphenylglycolic acid 4 and then reduced; Scheme 5 depicts the process in which the 5-cyclohexenyl-5-phenyldioxol-2-one 3 is first reduced to 5-cyclohexyl-5-phenyldioxol-2-one 5 and then reduced.

Scheme 4

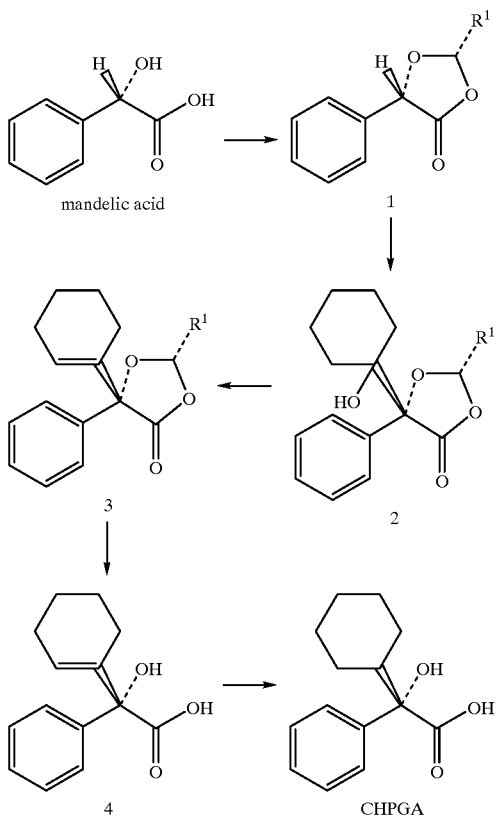

Scheme 5

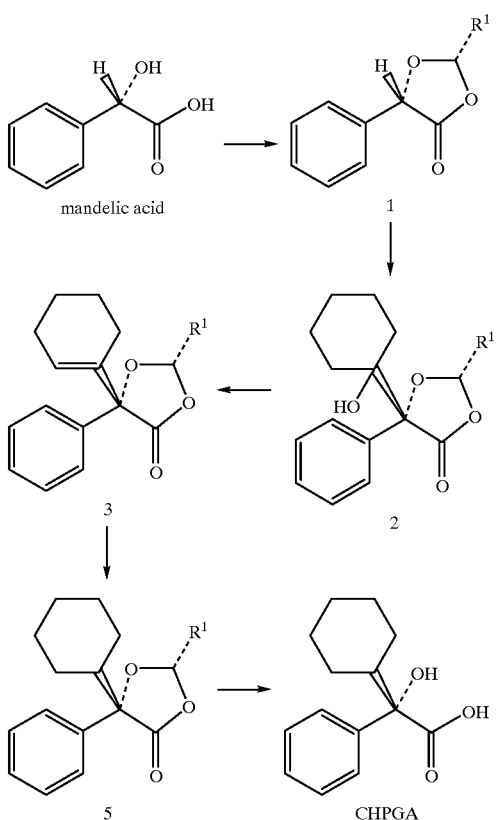

mandelic acid

CHPGA

According to the process depicted in both Scheme 4 and Scheme 5, an aldehyde R¹CHO is condensed with mandelic acid in the presence of an acid catalyst to provide a 5-phenyl-1,3-dioxolan-4-one 1. The preferred aldehydes for enantioselective syntheses are pivaldehyde and diphenylacetaldehyde. Acetone is preferred when the racemic synthesis is followed. The preferred acids for condensing aldehydes are sulfonic acids such as methanesulfonic acid, trifluoromethanesulfonic acid and toluenesulfonic acid; if acetone is used, sulfuric acid may be employed.

The 5-phenyl-1,3-dioxolan-4-one 1 is condensed with an alkyl ketone or alkyl aldehyde, in this case cyclohexanone, in the presence of a base to provide a 5-(1-hydroxyalkyl)-5-phenyl-1,3-dioxolan-4-one 2. Preferably the base is a lithium amide, such as lithium diethylamide or lithium bis(trimethylsilyl)amide. The best yields are obtained if the process is carried out below ambient temperature. In the case of the cyclohexanone adduct described in the schemes (in which $R^1$ is t-butyl), the initially formed (kinetically favored) 2S,5S dioxolone 2 is obtained if the reaction is carried out on the dioxolone 1 arising from S-mandelic acid at temperatures below –40° C., whereas the thermodynamically favored 2S,5R dioxolone 2 is obtained if the reaction is carried out on the dioxolone 1 arising from S-mandelic acid at temperatures above –20° C. Between –40 and –20, mixtures are obtained, so that the process is not attractive if one enantiomer is desired; if enantioselectivity is not an issue, any temperature below ambient could be used, although yields are better at lower temperatures. At –78° C., a 92% yield of SS product is obtained; at 0° C., a 64% yield of SR product is obtained. Thus, if one wished to obtain S-CHPGA, one could start with S-mandelic acid and carry out the aldol at –78° C. or one could start with R-mandelic acid and carry out the aldol at 0° C. The chemical yields appear better on the S to S process. Conversely, if one wished to obtain R-CHPGA, one could start with R-mandelic acid and carry out the aldol at –78° C. or one could start with S-mandelic acid and carry out the aldol at 0° C. The reaction is run in an inert solvent or solvent mixture having a freezing point below the desired temperature for the reaction. Typical solvents include lower alkanes, ethers and mixtures thereof.

The 5-(1-hydroxyalkyl)-5-phenyl-1,3-dioxolan-4-one 2 is subjected to dehydrating conditions to provide a 5-(1-alkenyl)-5-phenyl-1,3-dioxolan-4-one 3. Preferred dehydrating conditions are the sequential treatment with thionyl chloride and then pyridine, but any of the myriad of conditions known to persons in the art for converting alcohols to alkenes could be used. Other dehydrating reactions that may be employed include: formic acid [Wang et al *J. Chem. Soc.* 1949, 2186]; potassium bisulfate [Cook et al *J. Chem. Soc.* 1938, 58]; sulfuric acid [Lochte *J. Am. Chem. Soc.* 75, 4477 (1953)]; zinc chloride, oxalic acid and iodine [Criegee *Chem. Ber.* 85, 144 (1952)]; nitric acid [Nametkin *Chem. Ber.* 56, 1803 (1926)]; phosphoryl chloride [Sauers *J. Am. Chem. Soc.* 81, 4873 (1959)]; aluminum sulfate [Vogel *J. Chem. Soc.* 1938, 1323]; iodine [Sonawane et al. *Tetrahedron* 1986, 6673]; phosphorus oxychloride and pyridine [Campbell *J. Chem. Soc. B*, 1968, 349]; p-toluenesulfonic acid [Olah *J. Ore. Chem.* 55, 1792 (1990); and Humphreys *J. Chem. Soc. P1* 1978, 33]; N-bromosuccinimide [Taguchi *Tet. Lett.* 1973, 2463]; HCl [Maillard *Bull. Soc. Chim. Fr.* 1966, 1683]; and trifluoroacetic acid [Levin et al. *Tet. Lett.* 1985. 505].

As mentioned above, the dioxolan-4-one 3 may be first hydrolyzed and then reduced, as shown in Scheme 4, or first reduced and then hydrolyzed, as in Scheme 5. In either case, the hydrolysis is preferably carried out using aqueous alkali metal hydroxide in an alcoholic or polar aprotic solvent, for example, potassium hydroxide in methanol-water. Reduction is preferably accomplished by exposure to hydrogen gas in the presence of a noble metal catalyst. The hydrogen may be provided as gaseous hydrogen or may be derived by metathesis from a hydrogen source such as ammonium formate. The catalyst is preferably palladium on a solid support such as carbon, but one may also use other noble metal catalysts such as platinum and rhodium catalysts.

As will be evident from the examples below, it is not necessary to isolate and purify each intermediate, although this was done initially to guide the experimentation. The examples below are syntheses in which the alkyl ketone was cyclohexanone. As will be evident to the person of skill in the art, other ketones and aldehydes could be substituted for cyclohexanone to make other α-alkylphenylglycolic acids.

EXAMPLES

Process for Isolating Each Intermediate and Reducing Before Saponifying:

Cis-(2S,5S)-2-(tert-butyl)-5-phenyl-1,3-dioxolan-4-one (1): To a suspension of (S)-(+)-mandelic acid (10.0 g, 65.7 mmol) in pentane (150 mL) was added pivaldehyde (8.56 mL, 78.8 mmol), followed by addition of methanesulfonic acid (213 μL, 3.2 mmol) at rt. To the reaction flask was added a dean-stark trap, the mixture was warmed to 75° C. and allowed to reflux for 5.5 h. The reaction mixture was washed with water (2×150 mL), dried with sodium sulfate, and filtered. The filtrate was then concentrated in vacuo to provide a white solid. The crude material was dissolved in 50 mL of hot ethyl acetate and allowed to cool to 0° C. The solids formed were collected by filtration and dried to give 10.7 g (74%) of product. ¹H NMR (CDCl₃) δ 1.12 (s, 9H), 5.28 (s, 1H), 5.36 (s, 1H), 7.47 (m, 5H). $^{13}$C-NMR δ 23.80, 24.42, 34.64, 109.47, 127.23, 128.91, 129.35, 133.70, 172.04.

Cis-(2S,5S)-2-(tert-butyl)-5-phenyl-5-(cyclohexyl-1-ol)-1,3-dioxolan-4-one (2): To a −78° C. solution of Lithium bis-(trimethylsilyl)-amide (46.7 mL, 46.7 mmol, 1.0M in hexanes) in THF (250 mL) was added Cis-(2S,5S)-2-(tert-butyl)-5-phenyl-1,3-dioxolan-4-one (9.80 g, 44.5 mmol, dissolved in 80 mL THF). The reaction mixture was allowed to stir for 0.5 hours at −78° C., after which ccylohexanone (5.07 mL, 46.7 mmol) was added. After stirring for a further 2 hours at −78° C., a solution of saturated NH$_4$Cl solution (8.0 mL) was added. The reaction mixture was poured into a separatory funnel containing saturated NH$_4$Cl solution (300 mL). The aqueous layer was separated and washed with ethyl acetate (2×300 mL). The combined organic layers were dried (Na$_2$SO$_4$), filtered and concentrated in vacuo to provide 12.01 g of crude aldol product (85%) as a white solid. $^1$H NMR (CDCl$_3$) δ 0.95 (s, 9H), 1.38–1.98 (m, 10H), 5.53 (s, 1H), 7.39 (m, 3H), 7.76 (m 2H). $^{13}$C-NMR δ 21.14, 21.23, 23.59, 25.32, 30.99, 31.22, 35.69, 86.68, 111.10, 126.98, 127.66, 128.13, 135.42, 172.54.

Cis-(2S,5S)-2-(tert-butyl)-5-phenyl-5-(cyclohex-1-ene)-1,3-dioxolan-4-one (3): To a 0° C. solution of cis-(2S,5S)-2-(tert-butyl)-5-phenyl-5-(cyclohexyl-1-ol)-1,3dioxolan-4-one (12.0 g, 37.8 mmol) in THF (300 mL) was added pyridine (30.6 mL, 378 mmol) followed by Thionyl chloride (8.2 mL, 113.5 mmol.). The reaction mixture was allowed to stir for 1 h at 0° C. followed by the addition of saturated NH$_4$Cl solution (300 mL). The layers were separated and the aqueous layer was washed with ethyl acetate (2×200 mL). The combined organic layers were dried (Na$_2$ SO$_4$), filtered and concentrated in vacuo to provide 11.37 g of crude product (96%). $^1$H NMR (CDCl$_3$) δ 1.03 (s, 9H), 1.54–2.19 (m, 8H), 5.17 (s, 1H), 6.07 (m, 1H), 7.37 (m, 3H)k, 7.55 (m, 2H). $^{13}$C-NMR δ 22.10, 22.60, 23.78, 23.90, 24.43, 25.30, 34.45, 86.35, 107.38, 126.20, 127.48, 128.40, 132.66, 136.91, 171.86. Cis-(2S,5S)-2-(tert-butyl)-5-phenyl-5-(cyclohexyl)1,3-dioxolan-4-one (5): To a solution of Cis-(2S,5S)-2-(tert-butyl)-5-phenyl-5-(cyclohex-1-ene)-1,3-dioxolan-4-one (2.34 g, 7.8 mmol) in methanol (35 mL) was added 10% Pd/C (0.23g). The reaction was subjected to 1 ATM of Hydrogen and was allowed to stir for 6 h. The reaction mixture was filtered through a plug of celite and concentrated in vacuo to provide 2.2 1g of crude product (94%). $^1$H NMR (CDCl$_3$) δ 0.92 (s, 9H), 1.04–1.80 (m, 11), 5.39 (s, 1H), 7.34 (m, 3H), 7.65 (m, 2H). $^{13}$C-NMR δ 23.73. 26/13. 26/15. 26/28. 26/33. 28.23, 35.78, 48.61, 85.35, 110.83, 125.52, 127.73, 128.03, 138.03, 173.99.

(S)-CHPGA: To a solution of Cis-(2S,5S)-2-(tert-butyl)-5-phenyl-5-(cyclohexyl)-1,3-dioxolan-4-one (11.44 g, 37.9 mmol) in MeOH (105 mL) was added a 1.8M solution of KOH (105 mL, 5 eq.). The reaction was allowed to reflux for 2.5 h. After cooling to rt, the volatiles (MeOH) was removed in vacuo and the aqueous reaction mixture was washed with ethyl acetate (50 mL). The aqueous layer was acidified to ph=1 with 1N HCl and the resulting mixture was washed with ethyl acetate (2×200 mL). The combined organic layers were dried (Na$_2$SO$_4$), filtered, and concentrated in vacuo to provide 7.9g of crude (S)-CHPGA (89%, 91.6% e.e.).

The resulting off-white solid was dissolved in 36.4 mL of toluene at a temperature of 65° C. To this warm solution was added 42 mL of heptane over a 10 min. period using an overhead mechanical stirrer. The solution was allowed to slowly cool to 0° C. where white crystals were formed. After stirring at 0° C. for 1 h, the reaction contents were filtered to provide 6.0 g of(S)-CHPGA (67%, 99.8% e.e.). $^1$H NMR(CDCl$_3$) δ 1.01–1.82 (m, 1OH), 2.25 (m, 1H), 7.32 (m, 3H), 7.63 (m, 2H). $^{13}$C-NMR δ 25.57, 26.27, 26.42, 27.52, 81.15, 126.10, 127.85, 128.24, 140.03, 180.97.

Process With Saponification Before Reduction:

(S)-Cyclohexenyl phenyl glycolic acid (4): To a solution of cis-(2S,5S)-2-(tert-butyl)-5-phenyl-5-(cyclohex-1-ene)-1,3-dioxolan-4-one (2.9 g, 9.9 mmol) in THF (27 mL) was added a 1.8M solution of KOH (27 mL, 5 eq.). The reaction was allowed to reflux for 7 h. After cooling to rt, the reaction mixture was washed with heptane (75 mL×2). The aqueous layer was acidified to pH=1 with 1N HCl and the resulting mixture was washed with ethyl acetate (2×75 mL). The combined organic layers were dried (Na$_2$SO$_4$), filtered, and concentrated in vacuo to provide 1.19 g of crude (S)-Cyclohexenyl phenyl glycolic acid (51%, 98.3% e.e.). $^1$H NMR (CDCl$_3$) δ 1.04–1.68 (m, 4H), 2.00–2.09 (m, 4H), 5.70 (m, 1H), 7.27 (m, 3H), 7.56 (m, 2H). $^{13}$C-NMR δ 22.11, 22.97, 24.88, 25.46, 82.40, 127.12, 127.27, 128.22, 128.25, 138.05, 179.24.

(S)-CHPGA: To a solution of (S)-Cyclohexenyl phenyl glycolic acid (1.11 g, 4.78 mmol) in methanol (16 mL) was added 10% Pd/C (0.11 g). The reaction was subjected to 1 ATM of Hydrogen and was allowed to stir for 18 h. the reaction mixture was filtered through a plug of celite and concentrated in vacuo to provide 1.01 g of (S)-CHPGA (91%, 98.3% e.e.).

Process Combining Aldol, Elimination and Saponification Without Isolation:

Cis-(2S,5S)-2-(tert-butyl)-5-phenyl-1,3-dioxolan-4-one (SS)-1: To a suspension of (S)-(+)-mandelic acid (10.0 g, 65.7 mmol) in pentane (150 mL) was added pivaldehyde (8.56 mL, 78.8 mmol), followed by addition of methanesulfonic acid (213 μL, 3.2 mmol) at rt. To the reaction flask was added a dean-stark trap. The mixture was warmed to 65° C. and allowed to reflux for 5.5 h. The reaction mixture was allowed to cool to rt, ethyl acetate was added (200 mL) and the solution was washed with said NaHCO$_3$ solution (150 mL) and concentrated in vacuo to provide a white solid. The crude material was dissolved in 50 mL of hot ethyl acetate and allowed to cool to 0° C. The solids formed were collected by filtration and dried to give 9.95 g (69%) of product.

(S)-Cyclohexenyl phenyl glycolic acid (S)-4: To a −78° C. solution of lithium bis-(trimethylsilyl)-amide (147.6 mL, 147.6 mmol, 1.0M in hexanes) was added Cis-(2S,5S)-2-(tert-butyl)-5-phenyl-1,3-dioxolan-4-one (S,S)-1 (25.0 g, 113.5 mmol, dissolved in 172 mL THF). The reaction mixture was allowed to stir for 0.5 h at −78° C., followed by the addition of cyclohexanone (16.47 mL, 158.9 mmol). After 2 h at −78° C., thionyl chloride (28.97 mL, 397.2 mmol) was added, followed by pyridine (41.3 mL, 510.7 mmol) and the reaction stirred an additional 30 min at −78° C. The reaction mixture was slowly warmed to 0° C. and allowed to stir an additional 4 h, followed by the addition if KOH (99.5 g, 1.7 mol) dissolved in 120 mL of H$_2$O. The reaction mixture was distilled to remove 275 mL of solvent. To the reaction mixture was added 75 mL of MeOH and allowed to reflux for 6 h. the reaction was allowed to cool to rt and washed with heptane (100 mL×2). The aqueous layer was acidified with 6N HCl until pH=2. Brownish crystals were collected by filtration and allowed to dry in vacuo to provide 21.5 g (81%, 96.7% e.e.) of(S)-4.

CHPGA: To a solution of cis-($^2$S,5S)-2-(tert-butyl)-5-phenyl-5-(cyclohex-1-ene)-1,3-dioxolan-4-one (S)-4 (2.4 g, 10.3 mmol) in methanol (24 mL) was added 10% Pd/C (0.24 g). The reaction was subjected to 1 ATM of Hydrogen and was allowed to stir for 18 h. The reaction mixture was filtered through a plug of celite and 10 mL of MeOH was used to wash the filter cake. The solvent was distilled to a volume of 20 mL, after which 40 mL of toluene was added. this was repeated 3 times, with the last distillation resulting in 11 mL final volume of solvent (toluene). The mixture was warmed to 65° C. and 12.9 mL of heptane was added to it. The mixture was slowly cooled to rt, then 0° C. for 2 h. the crystals were collected via filtration and dried to provide 2.11 g of pure (S)-CHPGA (87%, 99% e.e.).

Process Combining Cyclization/aldol and Elimination/saponification Steps:

Cis-(2S,5S)-2-(tert-butyl)-5-phenyl-5-(cyclohexyl-1-ol)-1,3-dioxolan-4-one (S)-2: To a suspension of (S)-(+) mandelic acid (25.0 g, 164 mmol) in pentane (250 mL) was added pivaldehyde (21.3 mL, 196 mmol), followed by addition of trifluoromethanesulfonic acid (625 µL, 7.0 mmol) at room temperature. To the reaction flask was added a dean-stark trap. The mixture was warmed to 65° C. and allowed to reflux for 4 hours. After the reaction was judged complete, a sodium bicarbonate solution (13.77 g in 100 mL of water) was added, and the pentane was removed via distillation. The white solids formed were collected by filtration to give 34.2 g (95%) of product dioxolone (S,S)-1.

To a −78° C. solution of lithium bis(trimethylsilyl)amide (77.94 mL of 1.0M in hexanes, 77.94 mmol, ) was added (S,S)-1 (59.96 mmol, dissolved in 90.8 mL THF). The reaction mixture was allowed to stir for 0.5 h at −78° C., followed by the addition of cyclohexanone (8.70 mL, 83.9 mmol). The reaction was allowed to stir for an additional 2 h at −78° C., after which it was quenched with 13.2 mL of a 10% solution of $NaH_2PO_4$ containing 5% NaCl. The reaction mixture was quickly poured into a separatory funnel containing 10% $NaH_2PO_4$ (174 mL). The organic layer was separated and concentrated in vacuo to provide crude aldol product as a white solid. The white solid was dissolved in 135 mL of 1% THF in heptane at 80° C. The solution was allowed to slowly cool to 0° C. and stir for 2 hours, after which the white crystals were filtered and dried to provide 14.4 g of aldolate (S,S)-2 (76% yield, >99.9% d.e.).

To a 0° C. solution of (S,S)-2 (31.8 g, 100 mmol) in THEF (332 mL) was added thionyl chloride (21.2 mL, 291 mmol). After 10 min., pyridine (37.8 mL, 468 mmol) was added slowly at 0° C. The reaction mixture was allowed to stir for 15 min at 0° C., followed by the addition of saturated $NH_4Cl$ solution (250 mL). The bottom layer (aqueous) was removed and the top layer (organic) was treated with KOH (29.1 g, 520 mmol) in 120 mL of water. The reaction mixture was distilled to remove 300 mL of solvent. MeOH (60 mL) was added and the reaction was allowed to reflux for 2 hours at 95° C. The reaction was washed with heptane (60 mL) and the aqueous layer was acidified to pH=2 with 6N HCl. The white precipitate was collected via filtration and dried to provide 21.5 g of (S)-4 (93%, 99.96% e.e.).

To a solution of Cis-(2S,5S)-2-(tert-butyl)-5-phenyl-5-(cyclohex-1-ene)-1,3-dioxolan-4-one (S)-4 (18.0 g, 77.58 mmol) in methanol (100 mL) was added 10% Pd/C (0.54 g, 3 mole %). The reaction was subjected to 30 psi of hydrogen and was allowed to stir for 18 h. The reaction mixture was filtered through a plug of Solka Flok and 20 mL of MeOH was used to wash the filter cake. The solvent was distilled at 95° C. to a volume of 9 mL, after which 100 mL of $H_2O$ was slowly added. The mixture was slowly cooled to rt, then 0° C. for 2 h. The solids were collected via filtration and dried to provide 17.2 g of (S)-CBPGA (95%, 100%, e.e.) $[\alpha]_D^{20}$=+ 26.23 (c=0.017, ethanol).

Process for Racemic Synthesis:

2-(Dimethyl)-5-phenyl-1,3-dioxolan-4-one: A 100 mL round bottom flask was equipped with a stir bar and magnetic stirrer. (S)-mandelic acid (5.0 g, 32.8 mmol) and acetone (15 mL) were added at room temperature. The reaction mixture was cooled to −10° C., and to it was added $H_2SO_4$ (3.17 g, 32.8 mmol) dropwise. After 1 hour at −10° C., the reaction contents were poured into an ice-cold solution of $K_2CO_3$ (8.3 g in 60 mL of $H_2O$). The white precipitate was filtered and washed sequentially with 1N NaOH (20 mL) and $H_2O$ (20 mL). After drying overnight, 5.4 g (93%) of 2-(dimethyl)-5-phenyl-1,3-dioxolan-4-one was obtained as a white solid.

2-(Dimethyl)-5-phenyl-5-(cyclohexyl-1-ol)-1,3-dioxolan-4-one: To a −78° C. solution of lithium bis-(trimethylsilyl)amide (2.98 mL, 2.98 mmol, 1.0M in hexanes) in 16 mL of dry THF was added 2-(dimethyl)-5-phenyl-1,3-dioxolan-4-one (0.50 g, 2.84 mmol) dissolved in 3 mL of THF. The reaction mixture was allowed to stir for 0.5 h at −78° C., followed by the addition of cyclohexanone (0.32 mL, 3.2 mmol). After 1 h at −78° C., pyridine (2.29 mL, 28.4 mmol) was added, followed by the addition of $SOCl_2$ (0.31 mL, 4.26 mmol), and the reaction stirred an additional 30 min at −78° C. The reaction mixture was slowly warmed to 0° C. and allowed to stir an additional 1 h. The reaction mixture was poured into a separatory funnel containing saturated $NH_4Cl$ (10 mL). The THF layer was concentrated in vacuo and chromatographed with silica gel using 3% EtOAc/hexane as eluent to provide 0.495 g (64%) of pure 2-(dimethyl)-5-phenyl-5-(cyclohexyl-1-ol)-1,3-dioxolan-4-one.

Cyclohexenyl phenyl glycolic acid: To a solution of 2-(dimethyl)-5-phenyl-5-(cyclohexyl-1-ol)-1,3-dioxolan-4-one (0.285 g, 1.048 mmol) in MeOH (7 mL), was added a 1.8M solution of KOH (7 mL, 12 eq.). The reaction was allowed to reflux for 2 h. After cooling to rt, the reaction mixture was washed with $Et_2O$ (20 mL). The aqueous layer was acidified to pH=1 with 1N HCl and the resulting mixture was washed with ethyl acetate (30 mL). The organic layer was dried ($MgSO_4$), filtered, and concentrated in vacuo to provide 0.2 g of crude cyclohexenyl phenyl glycolic acid (82%) as a white solid.

CHPGA: To a solution of cyclohexenyl phenyl glycolic acid (0.15 g, 0.687 mmol) in methanol (5 mL) was added 10% Pd/C (0.03 g). The reaction was subjected to 1 ATM of Hydrogen and was allowed to stir for 18 h. The reaction mixture was filtered through a plug of celite and concentrated in vacuo to provide 142 mg of crude CHPGA (94%) as a white solid.

Process Employing Diphenylacetaldehyde as the Substituted Acetaldehyde:

Cis-(2S,5S)-2-(diphenylmethylene)-5-phenyl-1,3-dioxolan-4-one [1; $R^1$=CH(Ph)$_2$]: To a suspension of (S)-(+)- mandelic acid (3.0 g, 19.7 mmol) in pentane (60 mL) was added (2,2)-diphenylethanal (6.55 mL, 23.7 mmol), followed by addition of methanesulfonic acid (75 uL, 0.84 mmol) at rt. To the reaction flask was added a dean-stark trap. The mixture was warmed to 65° C. and allowed to reflux for 4.0 h. The reaction mixture was allowed to cool to rt, ethyl acetate was added (50 mL) and the solution was washed with saturated $NaHCO_3$ solution (50 mL) and concentrated in vacuo to provide a white solid. $^1$H NMR analysis of the crude material suggested 58:42 diastereoselectivity. The crude material was chromatographed with 2% EtOAc/hexane to obtain one diastereomer.

Cis-(2S,5S)-2-(diphenylmethylene)-5-phenyl-5-(cyclohexyl-1-ol)-1,3-dioxolan-4-one: To a −78° C. solution of lithium bis-(trimethylsilyl)amide (0.88 mL, 0.88 mmol, 1.0M in hexanes) was added cis-(2S,5S)-2-(diphenylmethylene)-5-phenyl-1,3-dioxolan-4-one (0.68 mmol) dissolved in 5 mL of THF. The reaction mixture was allowed to stir for 0.5 h at −78° C., followed by the addition of cyclohexanone (0.098 mL, 0.93 mmol). The reaction was allowed to stir for an additional 2 h at −78° C., after which it was quenched with saturated NH$_4$Cl solution (1.0 mL). The reaction mixture was quickly poured into a separatory funnel containing saturated NH$_4$Cl solution (15.0 mL). The organic layer was separated and concentrated in vacuo to provide 0.223 g crude aldol product as a white solid in 58% yield (42% s.m. remained). $^1$H NMR of the crude material suggested 78:22 diastereoselectivity.

What is claimed is:

1. A compound chosen from the group consisting of:

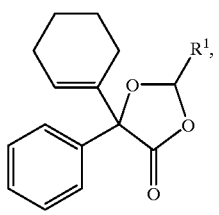 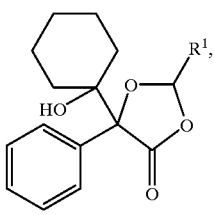

and

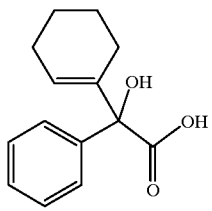

wherein R$^1$ is alkyl of 1 to 10 carbons or substituted alkyl of 4 to 20 carbon in total.

2. A compound according to claim 1 of formula

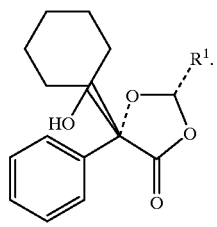

3. A compound according to claim 1 of formula

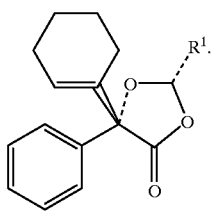

4. A compound according to claim 1 of formula

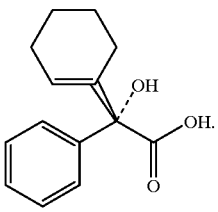

5. A compound according to claim 2 wherein R$^1$ is t-butyl.
6. A compound according to claim 3 wherein R$^1$ is t-butyl.

UNITED STATES PATENT AND TRADEMARK OFFICE
CERTIFICATE OF CORRECTION

PATENT NO.    : 6,376,684 B1
DATED         : April 23, 2002
INVENTOR(S)   : Senanayake et al.

It is certified that error appears in the above-identified patent and that said Letters Patent is hereby corrected as shown below:

Column 13,
Line 39, delete the word "carbon" and insert -- carbons --

Signed and Sealed this

Second Day of July, 2002

Attest:

Attesting Officer

JAMES E. ROGAN
Director of the United States Patent and Trademark Office